United States Patent [19]

Chance et al.

[11] Patent Number: 5,187,672

[45] Date of Patent: *Feb. 16, 1993

[54] PHASE MODULATION SPECTROSCOPIC SYSTEM

[75] Inventors: Britton Chance; Jian Weng, both of Philadelphia, Pa.

[73] Assignee: NIM Incorporated, Philadelphia, Pa.

[*] Notice: The portion of the term of this patent subsequent to Nov. 20, 2007 has been disclaimed.

[21] Appl. No.: 644,090

[22] Filed: Jan. 22, 1991

Related U.S. Application Data

[63] Continuation-in-part of Ser. No. 578,063, Sep. 5, 1990, Pat. No. 5,122,974, which is a continuation of Ser. No. 307,066, Feb. 6, 1989, Pat. No. 4,972,331.

[51] Int. Cl.$^5$ .......................... G06F 15/00; A61B 5/00
[52] U.S. Cl. .................................. 364/550; 128/633; 364/413.09
[58] Field of Search .................. 364/550, 525, 413.09, 364/497; 128/633

[56] References Cited

U.S. PATENT DOCUMENTS

| | | | |
|---|---|---|---|
| 4,138,727 | 2/1979 | Mantz | 364/525 |
| 4,714,341 | 12/1987 | Hamaguri et al. | 364/413.09 |
| 4,800,495 | 1/1989 | Smith | 364/413.09 |
| 4,800,885 | 1/1989 | Johnson | 364/413.09 |
| 4,824,242 | 4/1989 | Frick et al. | 364/413.09 |
| 4,846,183 | 7/1989 | Martin | 364/413.09 |
| 4,908,762 | 3/1990 | Suzuki et al. | 364/413.09 |
| 4,972,331 | 11/1990 | Chance | 364/550 |

OTHER PUBLICATIONS

Lackowicz, J. R., "Gigahertz Frequency-Domain Fluorometry: Resolution of Complex Intensity Decays, Picosecond Processes and Future Developments" Photon Migration in Tissues, Academic Press/N.Y., pp. 169-186 (1989).
Chance, B. et al., (1988) Proc. Natl. Acad. Sci. USA 85, pp. 4971-4975.
Chance, B. (Ed), "Photon Migration in Muscles and Brain," in Photon Migration in Tissues, Academic Press/New York, pp. 121-135 (1989).
Chance, B. (1951) Rev. Sci. Instrum. 22, 619-627.
Chance, B. (1966) Biochemistry of Copper, ed. Peisach, J. (Academic, New York), pp. 293-303.
Chance, B., Legallais, V. and Schoener, B. (1962) Nature (London) 195, 1073-1075.
Chance, B. (1954) Science 120, 767-775.
Chance, B. (1959) J. Biol. Chem. 234, 3036-3040.
Jobsis-VanderVlient, F. F. (1985) Adv. Exp. Med. Biol. 191, 833-842.
Jobis, F. F. et al., (1977) J. Appl. Physiol. 113, 858-872.
Rosenthal, M. et al., (1976) Brain Res. 108, 143-154.
vanderZee, P. et al. (1988) in Oxygen Transport to Tissue X, eds. Mochizuki, M. et al. (Plenum, New York) pp. 191-197.
Tamura, M. H. et al., (1987) in Chemoreceptors and Reflexes in Breathing, ed. Lahiri, S. (Oxford, N.Y.) in press.
Duysens, L. (1964) Prog. Biophys. Mol. Biol. 14, 1-104.
Chance, B. (1952) Nature (London) 169, 215-230.
Blumberg, W. E. (1987) Biophys. J. 51, 288 (abstr.).
Bonner, R. F. et al., (1987) J. Opt. Soc. Am. Sec. A 4, 423-432.
Galeotti et al. (Eds.), Membrane in Cancer Cells, 551 N.Y. Acad. Sci. (1988) (preface).

*Primary Examiner*—Kevin J. Teska
*Attorney, Agent, or Firm*—Fish & Richardson

[57] ABSTRACT

A phase modulated spectroscopy (PMS) system for detecting a pathophysiological condition in a subject includes two laser diodes emitting radiation at wavelengths of about 754-760 nm and 816-840 nm. These two laser diodes are modulated sinusoidally at about 220 MHz. The signals from each laser diode are brought to the subject by a bifurcated plastic optical fiber of 1 mm diameter. After transmission through the subject, the signals are detected by a Hamamatsu R928 photomultiplier (PMT), which generates two experimental signals. The experimental signals are compared to a reference signal in a phase detector. The respective phase shifts experienced by the signals are combined to form sum and difference signals, which are correlated to a pathophysiological condition.

37 Claims, 3 Drawing Sheets

1

PHASE MODULATION SPECTROSCOPIC SYSTEM

CROSS-REFERENCE TO RELATED APPLICATIONS

This application is a continuation-in-part of application Ser. No. 578,063, now U.S. Pat. No. 5,122,974 filed Sep. 5, 1990, which is a continuation of U.S. Pat. application No. 307,066, filed Feb. 6, 1989, now U.S. Pat. No. 4,972,331, issued on Jul., 25, 1990, all of which are incorporated by reference as if fully set forth herein.

BACKGROUND OF THE INVENTION

The present invention generally relates to the use of phase modulated spectroscopy (PMS) to to detect pathophysiological changes in a subject. More particularly, the present invention relates to methods and apparatuses for carrying out phase modulated spectroscopy. Still more particularly, the invention relates to improvements on the apparatuses disclosed in the above-referenced related applications.

The use of PMS to monitor the distribution of light pathlengths for detection of tissue absorption changes is discussed in the related applications. Further background is provided in Sevick, et al., "Analysis of Absorption, Scattering, and Hemoglobin Saturation Using Phase Modulation Spectroscopy," SPIE (1991), which is incorporated herein by reference. Briefly, the basis for using optical pathlength information to detect tissue absorption is that, as the absorption properties of a scattering medium increase (decrease), the probability of photons travelling long pathlengths within the medium decreases (increases), and therefore the mean optical pathlength travelled by the photons is reduced (increased).

SUMMARY OF THE INVENTION

The present invention provides a method for detecting a pathophysiological change in a subject. The method includes the steps of measuring the relative phase shift of, or change in effective optical path length $<L>$ traveled by, first and second electromagnetic signals transmitted through the subject, the signals having respective wavelengths causing them to be sensitive to hemoglobin deoxygenation and oxygenation; and then determining on the basis of the relative phase shifts or changes in $<L>$ the pathophysiological change in the subject. The relative phase shift or change in $<L>$ is preferably measured with a PMS system. As discussed below, the present invention is particularly useful in detecting a change in blood flow, tissue oxygen concentration, or ionic homeostasis.

The additional steps of correlating the phase shifts and/or changes in $<L>$ to hemoglobin deoxygenation and/or oxygenation in the subject, and correlating the hemoglobin deoxygenation and/or oxygenation to an intracellular event may be advantageously performed when carrying out the invention. The intracellular event may include a reduction of AND+ or a loss of electrical activity. When these additional steps are carried out, the invention is particularly useful in detecting an early warning of ischemic or hypoxic brain damage.

A preferred embodiment of the PMS system includes: first oscillator means for generating a first carrier waveform at a first frequency of at least 200 MHz; second oscillator means for generating a second carrier waveform at a second frequency offset approximately 25 KHz from the first frequency; means, coupled to the first oscillator means, for generating two electromagnetic signals modulated by the first carrier waveform, the two electromagnetic signals having different known wavelengths; means for coupling the electromagnetic signals to the subject; detector means for detecting two altered phase-shifted waveforms corresponding to the two electromagnetic signals, the altered signals having been phase-shifted during propagation through the subject; mixer means, coupled to the first and second oscillator means, for generating a reference signal having a frequency approximately equal to the difference between the first and second frequencies; and phase detector/filter means for generating a difference signal indicative of (i) the difference between the relative phases of the altered waveforms and/or (ii) the sum of the relative phases of the altered waveforms. The relative phases are determined with reference to the phase of the reference signal.

In its most preferred embodiment, the PMS system also includes AGC means for stabilizing the amplitudes of the altered waveforms before their relative phases are determined. In this embodiment, the AGC means comprises an MC1350 integrated circuit coupled to a feedback network; the phase detector/filter means comprises a 74HC221 integrated circuit coupled to a Schmitt trigger circuit for producing a square wave output signal, and the output signal is separated into signals indicative of the respective phase shifts undergone by the electromagnetic signals. In addition, the detector means includes a heterodyne modulation and mixing network having a resonant circuit providing a load impedance of approximately 20,000 ohms at 25 KHz.

DETAILED DESCRIPTION OF THE PREFERRED EMBODIMENT

Figure 1:
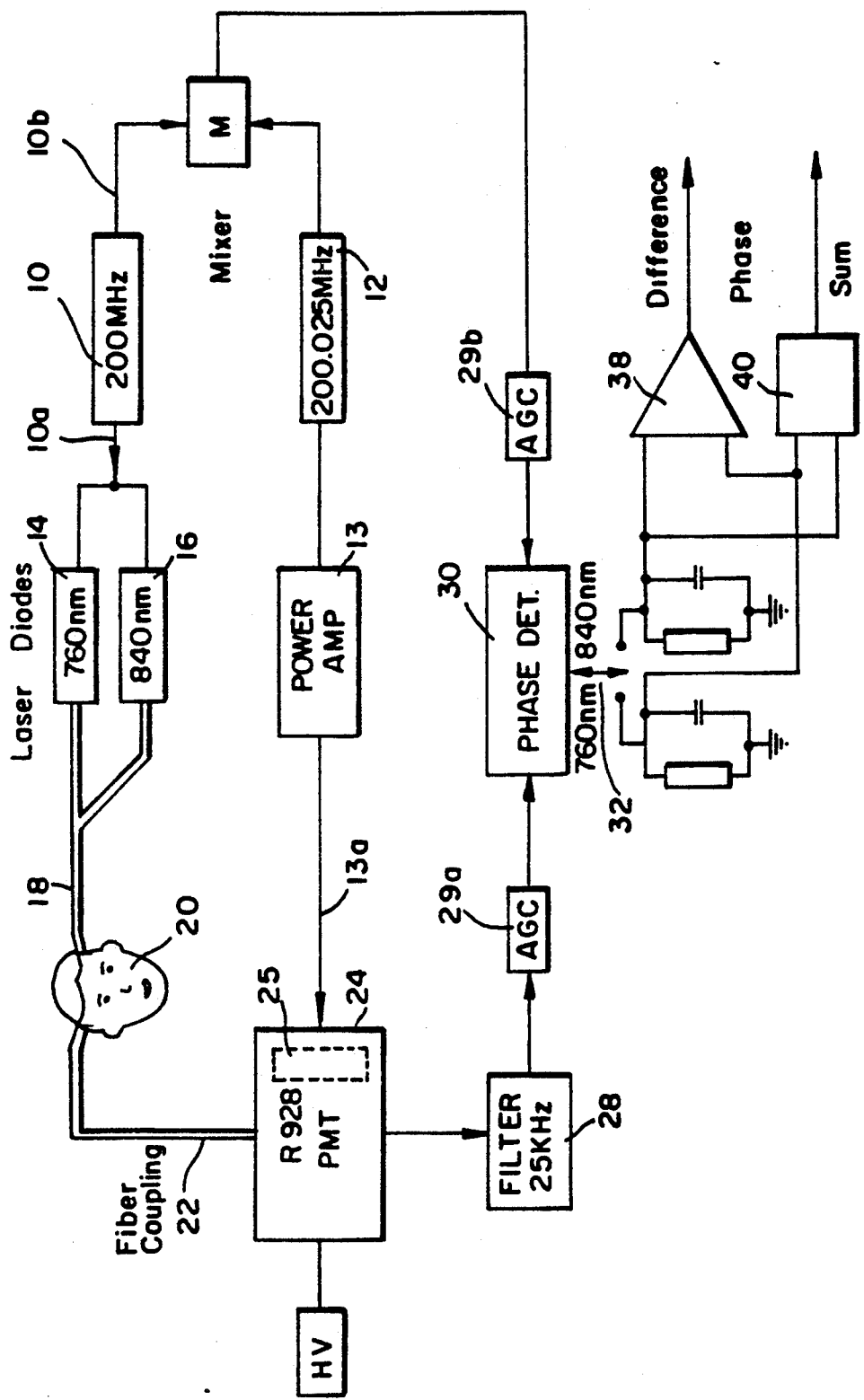
FIG. 1 is a block diagram of a dual wavelength PMS system in accordance with the present invention.

The invention was tested in a study reported in Maris et al., "Frequency Domain Measurements of Changes of Optical Pathlength During Spreading Depression in a Rodent Brain Model," SPIE (1991), which is incorporated by reference herein. The study will be described first and then the PMS system for carrying out the pathlength measurements will be described.

It is known that a near infrared phase modulated spectrophotometer provides a useful non-invasive tool to measure and monitor diseases that change tissue oxygenation by monitoring the tissue's absorption due to oxy- and deoxy-hemoglobin. The phase shift $\theta$ of emergent light relative to incident light can be measured with a system that emits light at wavelengths sensitive to hemoglobin deoxygenation (e.g., 754-760 nm) and oxygenation (e.g., 816-840 nm); therefore changes in hemoglobin oxygenation alter the distribution of the photon paths and shift the measured phase. $\theta$ is reported in terms of $<L>$, the effective pathlength, by using the relations $\theta=2\pi f<L>/nc$, where c is the speed of light($3*10^{10}$ cm/s), n is the refractive index of the medium (1.33 for an aqueous solution), and f is the modulation frequency (220 MHz). Changes in $<L>$ can be used to monitor changes in hemoglobin oxygenation and total hemoglobin concentration when measured at a wavelength that straddles the isosbestic point of hemoglobin (800 nm), e.g., at $\lambda=754$ nm and 816 nm. Thus hemoglobin saturation may be effectively monitored from the measured changes in $<L>$.

In the study, a dual wavelength PMS system was used to measure $<L>$ during changes in blood flow (ischemia), tissue oxygen concentration (hypoxia) and ionic hemeostasis (spreading depression) in rodent brains. In addition, measurements of $<L>$ were compared to measurements of tissue metabolism, electrical activity and blood flow. The changes in hemoglobin monitored by using light at 754 and 816 nm were found to correlate with intracellular events such as the reduction of $AND^+$ and the loss of electrical activity. See Mahevsky, Sclarsky, "Correlation of Brain NADH Redox State, $K+$, $PO_2$ and Electrical Activity During Hypoxia, Ischemia and Spreading Depression," Oxygen Transport to Tissue-IV, 129-141 (1983).

A rodent brain was chosen as the experimental model for two major reasons: it is a well characterized model, and the brain blood supply, oxygenation and ionic homeostasis can be easily manipulated. In addition, the carotid arteries can be readily isolated and occluded to induce ischemia and respiratory gases can be controlled to induce hypoxia.

Spreading depression (SD) is a unique brain phenomenon that is thought to be associated with migraine headaches. It is initiated by a localized infarct that results in depolarization of the neural and glial cell membranes of the outer cortex of the brain. The depolarization is characterized by a release of $K+$ from cells of the cortex and a shift of extracellular Na and Ca into the cells. The depolarization wave spreads from the infarct at a velocity of 3 mm/min and results in vasoconstriction and hypoperfusion in the outer cortex, followed by vasodilatation and greatly increased metabolic activity during polarization recovery. It has been found, however, that there is depressed blood flow by 20-25% for at least an hour after the SD. It has also been found that the extracellular space decreases during depolarization by as much as 50%. Since the vascular, metabolic and physical changes are unique during SD, the effects of SD on $<L>$ are quite different from the effects of hypoxia or ischemia on $<L>$; thus changes in $<L>_{754}$ and $<L>_{816}$ are useful in studying the physiological response of the brain to SD.

In this study, $<L>$ was compared to independent measurements of brain function to determine its utility as a brain monitoring parameter. During hypoxia and ischemia, deoxygenation is accompanied by a decrease in $<L>_{754}$ and an increase in $<L>_{816}$; reoxygenation is accompanied by an increase in $<L>_{754}$ and an increase in $<L>_{816}$. As total tissue blood volume increases, pathlengths at both wavelengths decrease, and as total tissue blood volume decreases, pathlengths increase. In the study, independent measurements of pathophysiology consisted of brain metabolism (NADH fluorescence), electrical activity (ECoG), and blood flow (doppler flow).

Briefly, the system used in the study included two laser diodes emitting radiation at wavelengths of 754 nm and 816 nm, although other wavelengths could have been used. The laser diodes were sinusoidally modulated at 220.010 MHz and 220.025 MHz. Light was brought to the rodents' brains from each laser diode with a bifurcated plastic optical fiber having a 1 mm diameter. Light transmitted through the subject was received by a 1 mm glass optical fiber and detected by a Hamamatsu R928 photomultiplier (PMT). Heterodyne mixing of a third 220 MHz oscillator signal with the 220.010 MHz and 220.025 MHz signals produced 10 KHz and 25 KHz reference signals. The 220 MHz signal was also coupled to the second dynode of the PMT to facilitate dynode mixing and generation of 10 KHz and 25 KHz experimental signals. The experimental signals were compared to the reference signals in a phase detector. The two output voltages from the phase detector represented the respective phase differences between the 754 nm and 816 nm experimental signals and the reference signal.

To calibrate the system, a voltage proportional to the phase shift of the emergent light relative to the incident light was recorded. To correlate the voltage to the change in phase, voltage measurements were recorded for various concentrations ($\mu s$) of a known scatterer. The known scatterer was a fat emulsion (Intralipid 20%) diluted to about the physiological scattering range (1%) to achieve a scattering concentration of 14.5 $cm^{-1}$ with negligible absorption. From the separations $\rho$, concentrations $\mu s$ and measured phase shifts $\theta$, $<L>$ can be calculated using the photon diffusion approximation. See Sevick, et al., "Non-invasive and Dynamic Measurement of Hemoglobin Saturation in Perfused Tumors. J. Cancer Research and Clinical Oncology, 116, S514 (1990). The slope (calculated using linear regression from the voltage and $<L>$ values measured during calibration) was used to calculate $<L>$ from voltages recorded during the experimental studies.

Each animal was anesthetized by intraperitoneal injection of Equi-Thesin (0.3 ml/100 g body weight). Each skull was surgically exposed and a 5 mm hole was made in the right parietal bone. The dura matter of the brain surface was carefully removed from the area where the $K+$ electrode was placed. A multiprobe assembly (MPA) (described below) was then placed above the cortex without putting pressure on the brain. Four steel screws were placed in the skull to provide an anchor. Ground and reference electrodes were placed below the skin and were cemented to the skull together with the MPA and the screws. The left and right carotid arteries were surgically exposed and sutures were placed around them to initiate ischemia. Nitrogen was used to initiate hypoxia. A topical application 0.5 M, 1.0 M of aqueous KCL was used to initiate SD. All probes were held in place by a Delrin canula, except the PMS detecting fiber which was placed 8 mm posterior and on the same hemisphere as the MPA. The MPA consisted of a delrin canula that held light guides for NADH fluorescence, doppler flow, and PMS light inputs. The details and operation of the MPA are described in U.S. Pat. application Ser. No 643,782, filed on Jan. 22, 1991 entitled "Methods and Apparatus for Intraoperative Monitoring of Brain Functions," which is incorporated herein by reference.

The intramitochondrial NADH redox state was monitored with a light guide fluorometer/reflectometer. The source for the 366 nm light was a 100-watt mercury arc cooled by air. The emitted light was split in a 90:10 ratio for measurement of the NADH fluorescence and reflectance, respectively. The light entered the tissue and was either reflected out of the tissue or absorbed by NADH, which then fluoresced at 435 nm. The ratio of the fluoresced and reflected light compensated for any blood volume changes in the tissue and provided a measurement of intramitochondrial NADH levels. The common part of the bifurcated light guide was cemented inside the MPA.

The doppler blood flow meter was a commercial model (manufactured by Transonics Inc., Ithaca, N.Y.) that emitted light at 633 nm. The doppler flow meter NIR light affected the FRS measurements by contributing a large DC light background to the PMT. This made it necessary to operate the FRS and doppler flow meter independently of each other.

The ECoG monitored each brain's electrical activity by measuring the DC and electrical changes of the outer surface of the brain cortex. A Ag/Cl wire was used to measure the DC potential while a series of stainless steel wires placed concentrically around the Ag/Cl were used to measure electrical activity.

Hypoxia, caused by 100% $N_2$ inspiration, caused a decrease in $<L>_{754}$ of 1 to 3 mm and an increase in $<L>_{816}$ of 1 to 2 mm. If the hypoxic/ischemic episode lasted for greater than 40 seconds, there was an overshoot in $<L>_{754}$ of about 1 mm that took 3–5 minutes to return to the baseline value. $<L>_{816}$ dropped by as much as 2 mm and took 2–5 minutes to recover to a baseline after restoration of $O_2$. The degree of change in $<L>$ varied between animals and during hypoxic episodes in the same animals.

The effects of hypoxia on ECoG and NADH were detected within 20 seconds. The NADH signal changed maximally in 55 seconds as the intramitochondrial $NAD^+$ became fully reduced to NADH. The ECoG signal dropped to zero at the same time the $NAD^+$ became fully reduced. The blood flow showed a change in 20 seconds and reached maximal flow at 80 seconds.

The effect of ischemia on $<L>$ was considerably less than the effect of hypoxia. The respective ranges of $<L>_{754}$ and $<L>_{816}$ prior to ischemia were 2.6–2.9 cm and 3.0–3.4 cm (the measurements were made with a source-detector separation of 8 mm). $<L>_{754}$ decreased by less than 1 mm and $<L>_{816}$ increased by about 1 mm during most ischemic episodes. During reflow of blood to the brain, $<L>_{754}$ returned to baseline; in contrast, $<L>_{816}$ often decreased below the baseline by a fraction of a mm.

Ischemia did not change the NAD signal until 20 seconds after the occlusion of the carotid arteries. Intracellular $O_2$ became completely depleted after this critical period, whereupon the NAD signal started to rapidly change as the NAD was reduced to NADH. After 40 seconds of bilateral ischemia the NAD was completely reduced to NADH. The rodent brain generally showed depressed electrical activity after changes in the NADH and $<L>$ were observed. The ECoG became depressed in 30 seconds and all electrical activity ceased in 45 seconds. The blood flow generally dropped to a minimal value after 20 seconds of bilateral occlusion. Reflow resulted in a transient increase in blood flow to the brain.

The depolarization phase of the SD wave caused a parallel increase of $<L>_{754}$ and $<L>_{816}$. The peak increase of $<L>$ for both wavelengths took 40–160 seconds and was about +2 mm. There was generally an undershoot in $<L>$ of about 2 mm that took 80–180 seconds. $<L>$ recovered to baseline after 240 seconds; however, the animal often experienced a series of SD waves that resulted in periods of increasing and decreasing $<L>$.

The goal of the study was to determine whether the changes in photon pathlengths at 754 at 816 nm are correlated with changes in local flow, electrical activity, and intracellular NADH levels within the cortex of a rodent brain insulted by hypoxia, ischemia, and SD. The results show that the changes in photon pathlengths during hypoxic and ischemic insults are indicative of deoxygenation of hemoglobin in the vascular space. It has also been found that the pathlength changes: (i) are correlated to changes in NADH levels (using ANOVA statistical tests), and (ii) precede the measured changes in intracellular NADH content and transmembrane potentials. In other words, deoxygenation of the vascular space preceded the intracellular response. The later finding confirms the important link between oxygen availability, metabolic energy, and the electrical potential gradient maintained by the $Na+ K+$ ATPase transmembrane pump. More importantly, these results indicate that PMS can accurately detect alteration in tissue oxygenation before actual insult to intracellular metabolic assemblies occur.

The results also show that changes in photon pathlengths caused by the wave of depolarization during SD are markedly different from changes caused by ischemic and hypoxic episodes. It has been observed that increases of photon pathlengths measured at both wavelengths as well as increased levels of NADH immediately following the depolarization wave as monitored with ECoG. This suggests SD causes either a decrease in total blood volume caused by vasoconstriction or an increase in the scattering properties of the cortex. Regardless, the results illustrate the ability of dual-wavelength PMS to discern pathophysiologic changes whether they entail changes in vascular volume or alteration in extracellular space.

A block diagram of an improved PMS system is shown in FIG. 1. The system includes master oscillator 10 operating at 200 MHz and master oscillator 12 operating at 200.025 MHz. Oscillator 10 directly drives two laser diodes 14, 16, which emit 760 nm and 840 nm light. The light source is time shared by small mirror excited by a 60 Hz chopper. The fiber optic coupler 18 between the laser diodes 14, 16 and the subject is nominally 3 mm; two 8 mm couplers 22 collect photons for the R928 PMT detector 24. The second dynode (not shown) of PMT 24 is modulated with a 200.025 MHz reference signal generated by amplifier 13; thus the PMT experiemntal signal will have a frequency of 25 KHz. The PMT 24 alternately detects the 760 nm and 840 nm light and produces corresponding output signals which are filtered by a filter 28 and leveled by the AGC circuit 29. A phase detector 30 generates a signal indicative of the phase of each output signal relative to the phase of a 25 MHz reference signal. The reference signal is produced by mixing the 200 and 200.025 MHz oscillator signals. The outputs of phase detector 30 are alternately selected by electronic switch 32, filtered, and then input to adder 40 and a subtracter 38 to produce sum and difference signals proportional to $<L>_{760} + <L>_{840}$ and $<L>_{760} - <L>_{840}$. The sum and difference signals are then used to calculate hemoglobin deoxygenation and blood volume.

Figure 2:
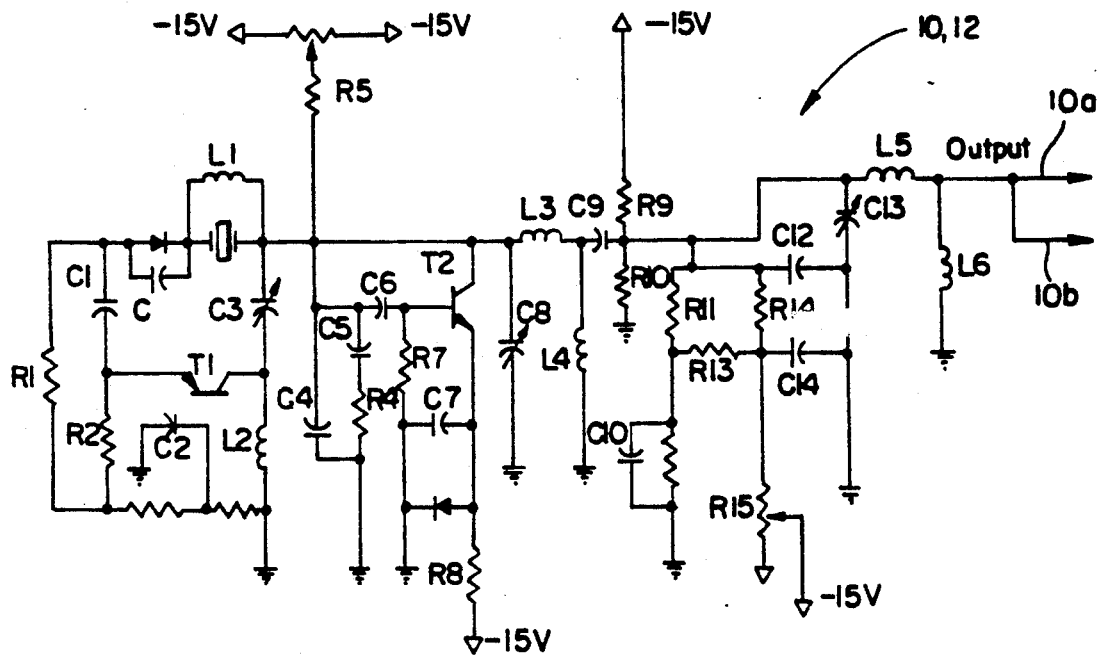
FIG. 2 is a schematic diagram of oscillator circuit 10 of FIG. 1.

A shematic diagram of a preferred oscillator 10, 12 is shown in FIG. 2. This circuit has a drift of only 0.03 degrees/hr. See Weng, et al., "Measurement of Biological Tissue Metabolism Using Phase Modulation Spectroscopic Measurement," SPIE, (1991), which is incorporated herein by reference. The crystal is neutralized which makes it possible to operate it at resonance, where long-term stability can be expected. The respective crystals of oscillators 10 and 12 are offset from each other by 25 KHz. This circuit provides sufficient output power to directly drive a 5 mw laser diode.

Figure 3:
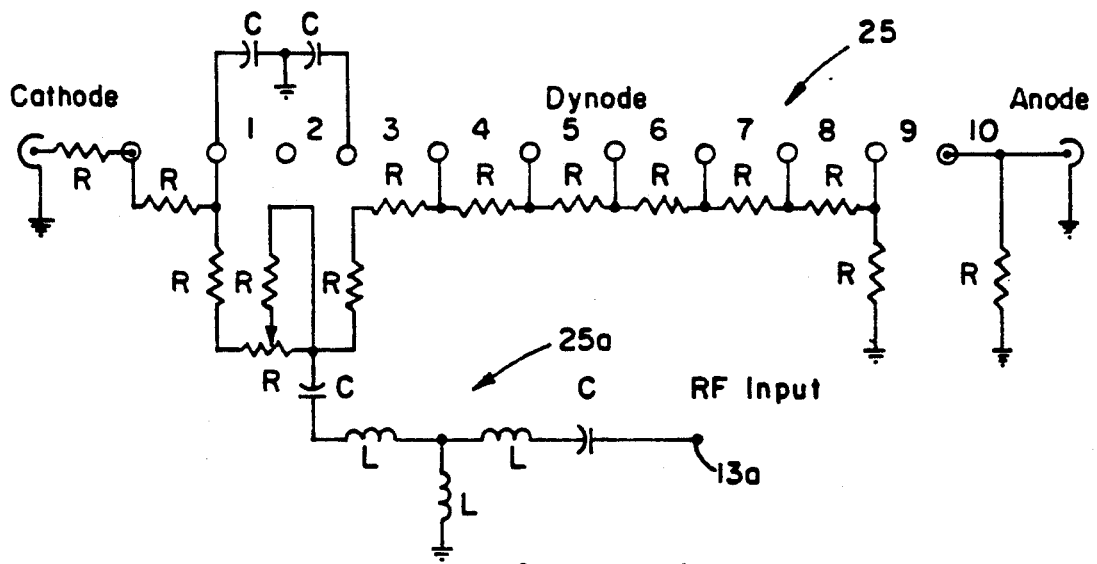
FIG. 3 is a schematic diagram of a PMT heterodyne modulation and mixing network in accordance with the present invention.

Another circuit, shown in FIG. 3, which presents a significant improvement over previously-used circuits is the modulation circuit 25 for dynode number 2 of the PMT 24. This circuit uses a resonant circuit 25a with an impedance of 20,000 ohms instead of the usual 50 ohm load with very high power dissipation, providing a 50 volt drive of the photomultiplier dynode while dissipating only a few watts of power.

Figure 4:
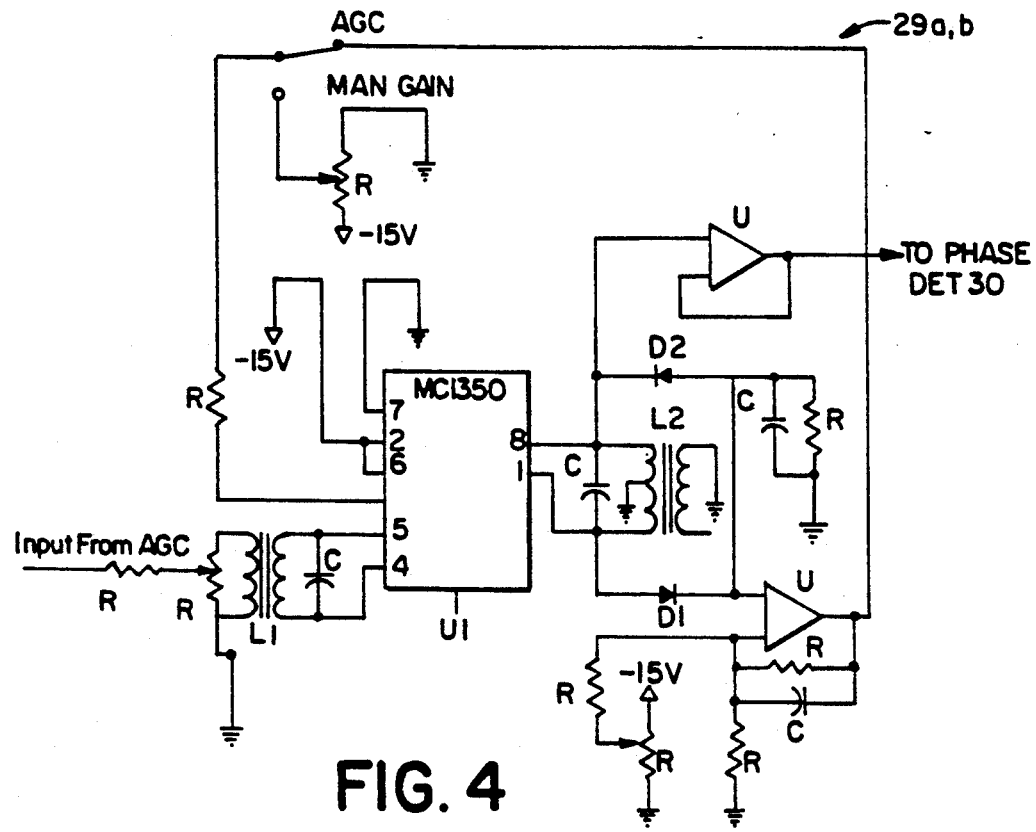
FIG. 4 is a schematic diagram of an AGC circuit in accordance with the present invention.

To obtain stable operation of the phase detector, a stable input signal is required. The 25 KHz AGC circuit 25 illustrated in FIG. 4 incudes an MC 1350 integrated circuit U1, featuring wide range AGC for use as an amplifier. The signal amplitude is controlled by a feedback network, as shown. A major reason why phase changes are accurately detected by the PMS system in accordance with this embodiment of the present invention is that the phase detector input signal level is nearly constant due to the AGC circuit.

The performance of the AGC circuit was evaluated to determine the effect of variations in the AC signal level upon the phase shift of the phase detector. A variation in the input voltage of between 2 and 6 volts was reflected in a variation in the phase shift of 0.2%; thus the AGC circuit eliminates the need for a very stable high voltage power supply.

Figure 5:
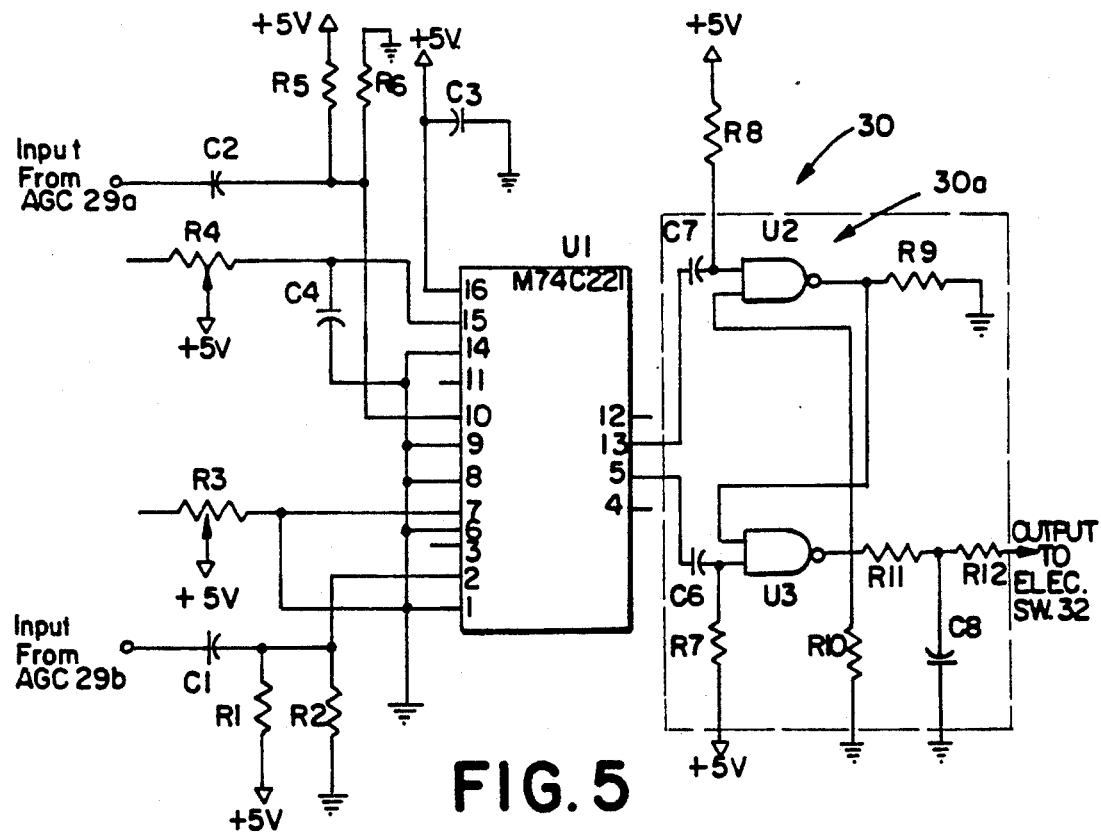
FIG. 5 is a schematic diagram of a phase detector circuit in accordance with the present invention.

A preferred phase detector circuit 30 is shown in FIG. 5. Two sinusoidal signals (the measurement signal and the reference signal) are transformed to a square wave signal by a Schmitt trigger circuit 30a. The phase of the square wave signal is shifted by an RC circuit (composed of R11, R12, C8), which make it possible to change the measuring range. The detector further includes a 74HC221 integrated circuit.

To calibrate the system, a blood yeast calibration method is applied. The ingredients for one serving of yeast calibration solution are:
5 grams yeast
20 ml 20% intralipid
10 ml fresh red blood cells
800 ml distilled water
3–4 drops of anti-foam.

When a baseline is reached, the first 2 ml of blood can be added to the suspension. The sum of the phase shifts indicates the blood volume change. It is then necessary to wait for another stable state. While oxygen is turned on and off, the difference between the two phase shifts indicates the concentration of deoxyhemoglobin and deoxymygolobin.

It should be noted that the true scope of the invention is not limited to the specific methods and apparatuses described above, but is set forth in the following claims.

What is claimed is:

1. A spectroscopic method for detecting at least one pathophysiological change in a subject, comprising the steps:
   (a) introducing into the subject, at an input port, first and second electromagnetic signals of wavelengths sensitive to hemoglobin oxygenation, said signals being modulated by a carrier waveform of frequency on the order of $10^8$ hz;
   (b) measuring the phase shift of said first and second electromagnetic signals that have migrated in the subject from said input to a detection port and
   (c) determining, on the basis of said relative phase shifts of said signal that have migrated in the subject said pathophysiological change in the subject.

2. The method recited in claim 1, wherein said pathophysiological change is a change in ionic homeostasis.

3. The method recited in claim 1, wherein the wavelength of said first electromagnetic signal is in the range of 754 to 60 nm.

4. The method recited in claim 1, wherein the wavelength of said second electromagnetic signal is in the range of 816 to 840 nm.

5. The method recited in claim 1, wherein the subject is a human.

6. The method recited in claim 1, wherein said pathophysiological change is a change in blood flow.

7. The method recited in claim 6, further comprising the step of detecting an early warning of ischemic brain damage.

8. The method recited in claim 1, wherein said pathophysiological change is a change in tissue oxygen concentration.

9. The method as recited in claim 8, further comprising the step of detecting an early warning of hypoxic brain damage.

10. The method recited in claim 1, further comprising the step of, prior to step (c), correlating said phase shifts to hemoglobin oxygenation in the subject.

11. The method recited in claim 10, further comprising the step of correlating hemoglobin oxygenation in the subject to an intracellular event.

12. The method recited in claim 11, wherein said intracellular event includes a reduction of NAD+.

13. The method recited in claim 11, wherein said intracellular event includes a loss of electrical activity.

14. The method recited in claim 1, wherein said introducing and measuring steps comprise:
   (a) generating a first carrier waveform at a first frequency of at least 200 MHz using first oscillator means;
   (b) generating a second carrier waveform at a second frequency using second oscillator means, said second frequency being offset approximately 25 KHz from said first frequency;
   (c) generating two electromagnetic signals modulated by said first carrier waveform, said two electromagnetic signals having different selected wavelengths sensitive to hemoglobin oxygenation;
   (d) coupling said two electromagnetic signals of said selected wavelengths to the subject;
   (e) detecting two altered phase-shifted waveforms corresponding to said two electromagnetic signals of said selected wavelengths, said altered signals having been phase-shifted during migration in the subject; and
   (f) measuring said phase shift of said two electromagnetic signals migrated in the subject.

15. The method recited in claim 1 or 14 wherein said determining step comprises
   (a) calculating an effective optical pathlength of photon migrating in said subject; and (b) correlating said pathlength to physiological properties of tissue of said subject through which said photons migrate.

16. A spectroscopic method for analyzing a scattering medium comprising at least one absorptive constituent, comprising:
   (a) generating a first carrier waveform at a first frequency of at least 200 MHz;
   (b) generating a second carrier waveform at a second frequency, said second frequency being offset on the order of 25 KHz from said first frequency;
   (c) generating two electromagnetic signals modulated by said first carrier waveform, said two electromagnetic signals having different selected wavelengths;
   (d) coupling said two electromagnetic signals of said selected wavelengths to the scattering medium;
   (e) detecting two altered phase-shifted waveforms corresponding to said two electromagnetic signals, said altered signals having been phase-shifted during migration in the scattering medium;
   (f) generating a reference signal having a frequency approximately equal to the difference between said first and second frequencies;
   (g) generating, at each said wavelength, a difference signal indicative of the phase-shift that is characteristic of said medium; and
   (h) determining, on the basis of said phase-shifts, selected property of the subject.

17. The method recited in claim 16, wherein the absorptive constituent is deoxy-hemoglobin.

18. The method recited in claim 16, wherein the absorptive constituent is oxy-hemoglobin.

19. The method recited in claim 16, further comprising the step of correlating the difference signal to hemoglobin oxygenation of the scattering medium.

20. The method recited in claim 19, wherein the scattering medium comprises a living tissue, and further comprising the step of correlating the hemoglobin oxygenation of the tissue to an intracellular event.

21. A phase modulation spectroscopic system for detecting at least one pathophysiological change in a subject, comprising:
   (a) means for introducing into the subject, at an input port, first and second electromagnetic signal of wavelengths sensitive to hemoglobin oxygenation, said signals being modulated by a carrier waveform of frequency on the order of at least $10^8$ Hz;
   (b) means for measuring the phase shift of said first and second electromagnetic signals that have migrated in the subject; and
   (c) means for determining, on the basis of said relative phase shifts of said signals that have migrated in the subject, said pathophysiological change in the subject.

22. The system recited in claim 21, wherein the subject is a human.

23. The system recited in claim 21, further comprising means for correlating said phase shifts to hemoglobin oxygenation in the subject, and providing a signal indicative of said hemoglobin oxygenation.

24. The system recited in claim 23, further comprising the means for correlating hemoglobin oxygenation in the subject to an intracellular event, and providing a signal indicative of said intracellular event.

25. The system recited in claim 24, wherein said intracellular event includes a reduction of NAD+.

26. The system recited in claim 24, wherein said intracellular event includes a loss of electrical activity.

27. A phase modulation spectroscopic system for analyzing a scattering medium comprising at least one absorptive constituent, comprising:
   (a) first oscillator means for generating a first carrier waveform at a first frequency of at least 200 MHz;
   (b) second oscillator means for generating a second carrier waveform at a second frequency offset on the order of 25 KHz from said first frequency;
   (c) light source means coupled to said first oscillator means, for generating two electromagnetic signals modulated by said first carrier waveform, said two electromagnetic signals having different selected wavelengths;
   (d) means for coupling said two electromagnetic signals of said selected wavelengths to the scattering medium;
   (e) detector means for detecting two altered phase-shifted waveforms corresponding to said two electromagnetic signals, said altered signals having been phase-shifted during migration in the scattering medium;
   (f) mixer means, coupled to said first and second oscillator means, for generating a reference signal having a frequency approximately equal to the difference between said first and second frequencies;
   (g) phase detector means for alternatively generating, at each wavelength, a difference signal indicative of of the phase shift that is characteristic of said medium; and
   (h) means for determining, on the basis of said phase-shifts, selected property of the subject.

28. The system recited in claim 27, wherein said phase detector means comprises a 74HC221 integrated circuit and a Schmitt trigger circuit for producing a square wave output signal.

29. The system recited in claim 27, wherein said detector means comprises a heterodyne modulation and mixing network having a resonant circuit providing a load approximately 20,000 ohms at 25 KHz.

30. The system recited in claim 27, further comprising automatic gain control means for stabilizing the amplitudes of said altered waveforms received from said detector means, said stabilized waveforms coupled to said phase detector means wherein said relative phases are determined.

31. The system recited in claim 30, wherein said automatic gain control means comprises an MC1350 integrated circuit coupled to a feedback network.

32. A spectroscopic method of examination of a subject, the subject lying between an optical input port and an optical detection port of a spectroscopic system, the optical pathlength of photons migrating between said ports being determined by the scattering and absorptive properties of the particular subject, the method comprising the steps of:
   (a) introducing into the subject at the input port at least one electromagnetic signal of selected wavelength, the signal having been modulated by a carrier waveform of frequency that enables determination of said pathlength;
   (b) detecting the signal at the detection port that has migrated in the path in the subject;
   (c) comparing the detected signal with the introduced signal and determining therefrom the phase shift of said detected signal from said introduced signal, said phase shift being indicative of said scattering and absorptive properties of the subject; and (d) examining said subject by employing said phase shift.

33. The method of claim 32 wherein said step of employing said phase shift comprises:
   (a) calculating, based on said phase shift, said optical pathlength of said signal between said optical input port and said optical detection port; and
   (b) determining a property of said subject based upon said pathlength.

34. The method of claim 32 or 33 wherein at least two electromagnetic signals of different selected wavelengths, modulated at said frequency, are introduced into the subject, and said step of examining said subject by employing said phase shift being performed utilizing each of said wavelengths.

35. The method of claim 34 wherein said introducing and detecting steps comprise:
   (a) generating a first carrier waveform at a first frequency on the order of $10^8$ Hz using first oscillator means;
   (b) generating a second carrier waveform at a second frequency using second oscillator means, said second frequency being offset from said first frequency;
   (c) generating two electromagnetic signals modulated by said first carrier waveform, said two electromagnetic signals having different selected wavelengths sensitive to hemoglobin oxygenation;
   (d) coupling said two electromagnetic signals of said selected wavelengths to the subject; and
   (e) detecting two altered phase-shifted waveforms corresponding to said two electromagnetic signals of said selected wavelengths, said altered signals having been phase-shifted during migration in the subject.

36. The method of claim 33 wherein said wavelength is selected from the region of about 750 nm to 850 nm.

37. The method of claim 32, 33 or 36 wherein said subject comprises tissue of a living being, said frequency of said carrier waveform is of the order of $10^8$ Hz, and said method comprising in vivo examination of said tissue.

* * * * *

UNITED STATES PATENT AND TRADEMARK OFFICE
CERTIFICATE OF CORRECTION

PATENT NO. : 5,187,672
DATED : February 16, 1993
INVENTOR(S) : Britton Chance, et. al.

It is certified that error appears in the above-indentified patent and that said Letters Patent is hereby corrected as shown below:

Column 1, line 60, "AND+" should be --NAD+--;
Column 3, line 22, "AND+" should be --NAD+--;
         line 40, "Na" should be --Na+--;
Column 6, line 54, "periemntal" should be --perimental--;
Column 7, line 59, "deoxymygolobin" should be --deoxymyoglobin--;
Column 8, line 14, "60nm" should be --760nm--.

Signed and Sealed this

Seventh Day of June, 1994

BRUCE LEHMAN

Attest:

Attesting Officer

Commissioner of Patents and Trademarks